(12) United States Patent
Jones et al.

(10) Patent No.: US 7,576,043 B2
(45) Date of Patent: *Aug. 18, 2009

(54) VISCOELASTIC WELLBORE FLUID COMPRISING AN ANIONIC SURFACTANT

(75) Inventors: Timothy Gareth John Jones, Cottenham (GB); Gary John Tustin, Sawston (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/675,355

(22) Filed: Feb. 15, 2007

(65) Prior Publication Data

US 2007/0197404 A1 Aug. 23, 2007

Related U.S. Application Data

(63) Continuation of application No. 10/343,401, filed on Oct. 15, 2003, now Pat. No. 7,196,041.

(30) Foreign Application Priority Data

Aug. 7, 2000 (GB) .................................. 0019381.3
Jul. 11, 2001 (WO) ..................... PCT/GB01/03123

(51) Int. Cl.
*C09K 8/584* (2006.01)
*E21B 43/00* (2006.01)

(52) U.S. Cl. ..................... 507/259; 507/265; 507/256

(58) Field of Classification Search ................. 507/135, 507/138, 256, 259, 265
See application file for complete search history.

(56) References Cited

U.S. PATENT DOCUMENTS

| | | | |
|---|---|---|---|
| 2,717,887 A | 9/1955 | Saner |
| 3,053,868 A | 9/1962 | Schmerling et al. |
| 3,408,373 A | 10/1968 | Ault et al. |
| 3,793,218 A | 2/1974 | Canevari |
| 4,556,495 A | 12/1985 | Shaw |
| 4,561,501 A | 12/1985 | Shaw et al. |
| 4,735,731 A | 4/1988 | Rose et al. |
| 4,799,549 A | 1/1989 | Vinot et al. |
| 4,931,216 A | 6/1990 | Igarashi et al. |
| 5,002,126 A | 3/1991 | Carlberg et al. |
| 5,551,516 A | 9/1996 | Norman et al. |
| 5,654,453 A | 8/1997 | Mueller et al. |
| 6,232,274 B1 | 5/2001 | Hughes et al. |
| 6,248,699 B1 | 6/2001 | Subramanian et al. |

FOREIGN PATENT DOCUMENTS

| | | |
|---|---|---|
| EP | 0 435 444 A1 | 7/1991 |
| GB | 2 332 223 A | 6/1999 |
| GB | 2 335 428 A | 9/1999 |
| GB | 2 335 680 A | 9/1999 |
| JP | 56169641 A | 12/1981 |
| WO | 85/02173 A1 | 5/1985 |
| WO | 93/04150 | 3/1993 |
| WO | 93/22270 A1 | 11/1993 |
| WO | 99/20722 A2 | 4/1999 |
| WO | 99/49183 A1 | 9/1999 |
| WO | 99/50530 A1 | 10/1999 |

OTHER PUBLICATIONS

Cates et al Statics and dynamics of worm-like surfactant micelles J. Phys. Condens. Matter, vol. 2, 1990, pp. 6869-6892.
Hoffman et al Gels from surfactant solutions with densely packed multilamellar vesicles Faraday Discuss, vol. 101, 1995, pp. 319-333.
Hoffman et al Surfactants, micelles and fascinating phenomena Angew. Chem.. Int. Ed. Engl., vol. 27, 1988, pp. 902-912.
Manoj et al Physicochemical studies on reverse micelles of sodium bis(2-ethylhexyl) sulfosuccinate at low water content Langmuir, vol. 12, 1996, pp. 4068-4072.
Rose, G. D. and Teot, A. S. Viscoelastic surfactants: rheology control without polymers or particulates Structure and Flow in Surfactant Solutions, Herb, C. A. and Prud'homme, R. K. (eds.), ACS Symposium Ser. 578, American Chemical Society, Washington D.C., 1994, pp. 352-369.
Samuel et al Polymer-free fluid for hydraulic fracturing SPE Annual Technical Conference and Exhibition, San Antonio, Texas, Oct. 5-8, 1997, SPE 38622.
Starks et al Use of quaternary salts as phase-transfer catalysts Phase-transfer catalysis, Fundamentals, Applications and Industrial Perspectives, Chapman and Hall, New York, 1994, pp. 125-153.

*Primary Examiner*—Timothy J. Kugel
(74) *Attorney, Agent, or Firm*—Edward Bushard; Steven Gahlings; James McAleenan

(57) ABSTRACT

A wellbore fluid comprising a surfactant, the surfactant having the formula $(R_1-X)_nZ$, wherein $R_1$ is an aliphatic group—comprising a $C_{18}$-$C_{22}$ principal straight chain bonded at a terminal carbon atom thereof to X, and comprising at least one $C_1$-$C_2$ side chain—X is a charged head group, Z is a counterion, and n is an integer which ensures that the surfactant is charge neutral, and wherein the charged head group X is selected to provide that the surfactant is soluble in oil and at least one part of the charged head group is anionic.

5 Claims, 5 Drawing Sheets

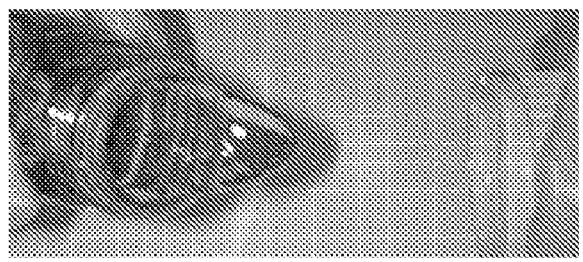
Code 4 Deformable non-flowing gel
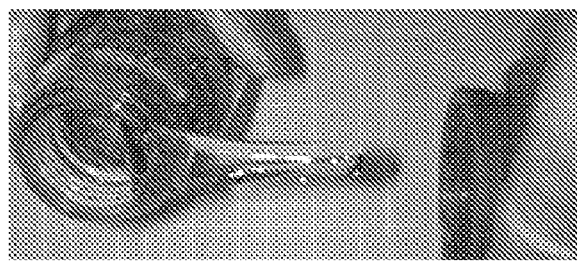
Code 3 Tonguing gel
Fig. 5
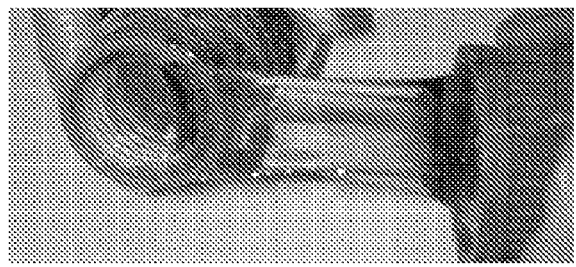
Code 2 Weak flowing gel
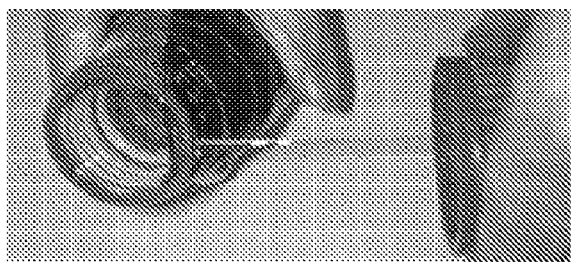
Code 1 Original viscosity

VISCOELASTIC WELLBORE FLUID COMPRISING AN ANIONIC SURFACTANT

This application claims the benefit of and is a continuation of U.S. application Ser. No. 10/343,401 U.S. Pat. No. 7,196,041 filed on Oct. 15, 2003, which is incorporated by reference in its entirety for all purposes.

FIELD OF THE INVENTION

The present invention relates to a surfactant, and in particular to a surfactant thickening agent for use in hydrocarbon recovery.

BACKGROUND OF THE INVENTION

In the recovery of hydrocarbons, such as oil and gas, from natural hydrocarbon reservoirs, extensive use is made of wellbore fluids such as drilling fluids, completion fluids, work over fluids, packer fluids, fracturing fluids, conformance or permeability control fluids and the like.

In many cases significant components of wellbore fluids are thickening agents, usually based on polymers or viscoelastic surfactants, which serve to control the viscosity of the fluids. Typical viscoelastic surfactants are N-erucyl-N,N-bis(2-hydroxyethyl)-N-methyl ammonium chloride and potassium oleate, solutions of which form gels when mixed with corresponding activators such as sodium salicylate and potassium chloride.

The surfactant molecules are characterized by having one long hydrocarbon chain per surfactant headgroup. In the viscoelastic gelled state these molecules aggregate into worm-like micelles. Gel breakdown occurs rapidly when the fluid contacts hydrocarbons which cause the micelles to change structure or disband.

In practical terms the surfactants act as reversible thickening agents so that, on placement in subterranean reservoir formations, the viscosity of a wellbore fluid containing such a surfactant varies significantly between water- or hydrocarbon-bearing zones of the formations. In this way the fluid is able preferentially to penetrate hydrocarbon-bearing zones.

The use of viscoelastic surfactants for fracturing subterranean formations is discussed in EP-A-0835983.

A problem associated with the use of viscoelastic surfactants is that stable oil-in-water emulsions are often formed between the low viscosity surfactant solution (i.e. broken gel) and the reservoir hydrocarbons. As a consequence, a clean separation of the two phases can be difficult to achieve, complicating clean up of wellbore fluids. Such emulsions are believed to form because conventional wellbore fluid viscoelastic surfactants have little or no solubility in organic solvents.

A few anionic surfactants exhibit high solubility in hydrocarbons but low solubility in aqueous solutions. A well known example is sodium bis(2-ethylhexyl) sulphosuccinate, commonly termed aerosol OT or AOT (see K. M. Manoj et al., *Langmuir*, 12, 4068-4072, (1996)). However, AOT does not form viscoelastic solutions in aqueous media, e.g. the addition of salt causes precipitation.

A number of cationic surfactants, based on quaternary ammonium and phosphonium salts, are known to exhibit solubility in water and hydrocarbons and as such are frequently used as phase-transfer catalysts (see C. M. Starks et al., *Phase-Transfer Catalysis*, pp. 125-153, Chapman and Hall, New York (1994)). However, those cationic surfactants which form viscoelastic solutions in aqueous media are poorly soluble in hydrocarbons, and are characterized by values of $K_{ow}$ very close to zero, $K_{ow}$ being the partition coefficient for a surfactant in oil and water ($K_{ow}=C_o/C_w$, where $C_o$ and $C_w$ are respectively the surfactant concentrations in oil and water). $K_{ow}$ may be determined by various analytical techniques, see e.g. M. A. Sharaf, D. L. Illman and B. R. Kowalski, *Chemometrics*, Wiley Interscience, (1986), ISBN 0471-83106-9.

Typically, high solubility of the cationic surfactant in hydrocarbon solvents is promoted by multiple long-chain alkyl groups attached to the head group, as found e.g. in hexadecyltributylphosphonium and trioctylmethylammonium ions. In contrast, cationic surfactants which form viscoelastic solutions generally have only one long unbranched hydrocarbon chain per surfactant headgroup.

The conflict between the structural requirements for achieving solubility in hydrocarbons and for the formation of viscoelastic solutions generally results in only one of these properties being achieved.

SUMMARY OF THE INVENTION

An object of the present invention is to provide a surfactant which is suitable for reversibly thickening water-based wellbore fluids and is also soluble in both organic and aqueous fluids.

A first aspect of the present invention provides a surfactant having the formula $(R_1-X)_nZ$. $R_1$ is an aliphatic group comprising a principal straight chain bonded at a terminal carbon atom thereof to X, the straight chain having a length such that a viscoelastic gel is formable by the surfactant in aqueous media; and further comprising at least one side chain (the carbon atoms of the side chain not being counted with the carbon atoms of the principal straight chain) which is shorter than said principal straight chain, said side chain enhancing the solubility of the surfactant in hydrocarbons, and being sufficiently close to said head group and sufficiently short such that the surfactant forms micelles in said viscoelastic gel. X is a charged head group, Z is a counterion, and n is an integer which ensures that the surfactant is charge neutral. Preferably the principal straight chain is a $C_{16}$-$C_{24}$ straight chain. Preferably the side chain is a $C_1$-$C_2$ side chain.

X may be a carboxylate (—COO$^-$), quaternary ammonium (—NR$_2$R$_3$R$_4^+$), sulphate (—OSO$_3^-$), or sulphonate (—SO$_3^-$) charged group; N being a nitrogen atom, and R$_2$, R$_3$ and R$_4$ being C$_1$-C$_6$ aliphatic groups, or one of R$_2$, R$_3$ and R$_4$ being a C$_1$-C$_6$ aliphatic group and the others of R$_2$, R$_3$ and R$_4$ forming a five-or six-member heterocylic ring with the nitrogen atom.

When X is a carboxylate, sulphate, or sulphonate group, Z may be an alkali metal cation (in which case n is one) or an alkaline earth metal cation (in which case n is two). Preferably Z is Na$^+$ or K$^+$.

When X is a quaternary ammonium group, Z may be a halide anion, such as Cl$^-$ or Br$^-$, or a small organic anion, such as a salicylate. In both these cases n is one.

Preferably the principal straight chain is a $C_{16}$-$C_{24}$ chain. More preferably it is a $C_{18}$ or a $C_{22}$ chain.

We have found that surfactants of this type are suitable for use as wellbore thickening agents, being soluble in both water and hydrocarbon-based solvents but retaining the ability to form aqueous viscoelastic solutions via micellar aggregation. This combination of properties is believed to be caused by the branching off from the principal straight chain of the C$_1$-C$_6$ side chain. The side chain apparently improves the solubility in hydrocarbon solvents by increasing the hydrophobicity of the R$_1$ aliphatic group.

By "viscoelastic", we mean that the elastic (or storage) modulus G' of the fluid is greater than the loss modulus G" as measured using an oscillatory shear rheometer (such as a Bohlin CVO 50) at a frequency of 1 Hz. The measurement of these moduli is described in *An Introduction to Rheology*, by H. A. Barnes, J. F. Hutton, and K. Walters, Elsevier, Amsterdam (1997).

In use, the enhanced solubility of the surfactant in hydrocarbon-based solvents can reduce the tendency for an emulsion to form between reservoir hydrocarbons and a broken surfactant gel based on the surfactant. It may also inhibit the formation of emulsions by natural surfactants in crude oil, such as naphthenic acids and asphaltenes. Additionally, dissolution of at least some of the surfactant molecules into the reservoir hydrocarbons can speed up breakdown of the gel.

Preferably, the side chain is a $C_1$-$C_2$ chain. We have found that, surprisingly, the solubility of the surfactant in hydrocarbon tends to increase as the size of the side chain decreases. We believe this is because smaller side chains cause less disruption to the formation of inverse micelles by the surfactant in the hydrocarbon, such inverse micelles promoting solubility in the hydrocarbon.

By altering the degree and type of branching from the principal straight chain, the surfactant can be tailored to be more or less soluble in a particular hydrocarbon. However, preferably the side chain is bonded to said terminal ($\alpha$), neighbouring ($\beta$) or next-neighbouring ($\gamma$) carbon atom of the principal chain. More preferably it is bonded to the $\alpha$ carbon atom. We believe that locating the side chain close to the charged head group promotes the most favourable combinations of viscoelastic and solute properties.

Preferably the side chain is a methyl or ethyl group. There may be two side groups, e.g. a methyl and an ethyl group bonded to the $\alpha$ carbon atom.

The principal straight chain may be unsaturated.

Preferably the surfactant is an alkali metal salt of 2-methyl oleic acid or 2-ethyl oleic acid.

A second aspect of the invention provides a viscoelastic surfactant having a partition coefficient, $K_{ow}$, of at least 0.05, $K_{ow}$ being measured at room temperature with respect to heptane and water. More desirably $K_{ow}$ is in the range from 0.05 to 1 and most desirably it is in the range 0.05 to 0.5. The surfactant may be a surfactant of the first aspect of the invention.

A third aspect of the invention provides an acid surfactant precursor to the surfactant of the first aspect of the invention, the acid surfactant precursor having the formula $R_1$—Y. $R_1$ is an aliphatic group comprising a $C_{10}$-$C_{25}$ principal straight chain bonded at a terminal carbon atom thereof to Y, and comprising at least one $C_1$-$C_2$ side chain. Y is a carboxylate (—COOH), sulphate (—$OSO_3H$), or sulphonate (—$SO_3H$) group.

In solution, acid surfactant precursors can be converted to the salt form, e.g. by neutralisation with the appropriate alkali or by the addition of the appropriate salt, to form surfactants of the first aspect of the invention.

A fourth aspect of the present invention provides a wellbore fluid comprising:
(a) water,
(b) a thickening amount of the surfactant of the first or second aspect of the invention, and
(c) an effective amount of a water-soluble, inorganic salt thickening activator.

Preferably the thickening activator is an alkali metal salt, such as KCl.

The surfactant is typically present in the fluid in a concentration of from 0.5 to 10 wt % (and more typically 0.5 to 5 wt %) and the thickening activator is typically present in the fluid in a concentration of from 1 to 10 wt %.

Desirably the wellbore fluid has a gel strength in the range 3 to 5 at room temperature, the gel strength falling to a value of 1 on contact with hydrocarbons such as heptane.

Desirably the wellbore fluid has a viscosity in the range 20 to 1000 (preferably 100 to 1000) centipoise in the shear rate range 0.1-100 (preferably 0.1-1000) $s^{-1}$ at 60° C., the viscosity falling to a value in the range 1 to 200 (preferably 1 to 50) centipoise on contact with hydrocarbons such as heptane, the viscosity being measured in accordance with German DIN standard 53019.

A fifth aspect of the present invention provides for use of the wellbore fluid of the fourth aspect of the invention as a fracturing fluid, a lubricant or an emulsion breaker.

BRIEF DESCRIPTION OF THE DRAWINGS

Specific embodiments of the present invention will now be described with reference to the following drawings in which:

FIG. 5 shows gel strength codings.

DETAILED DESCRIPTION

Figure 1:
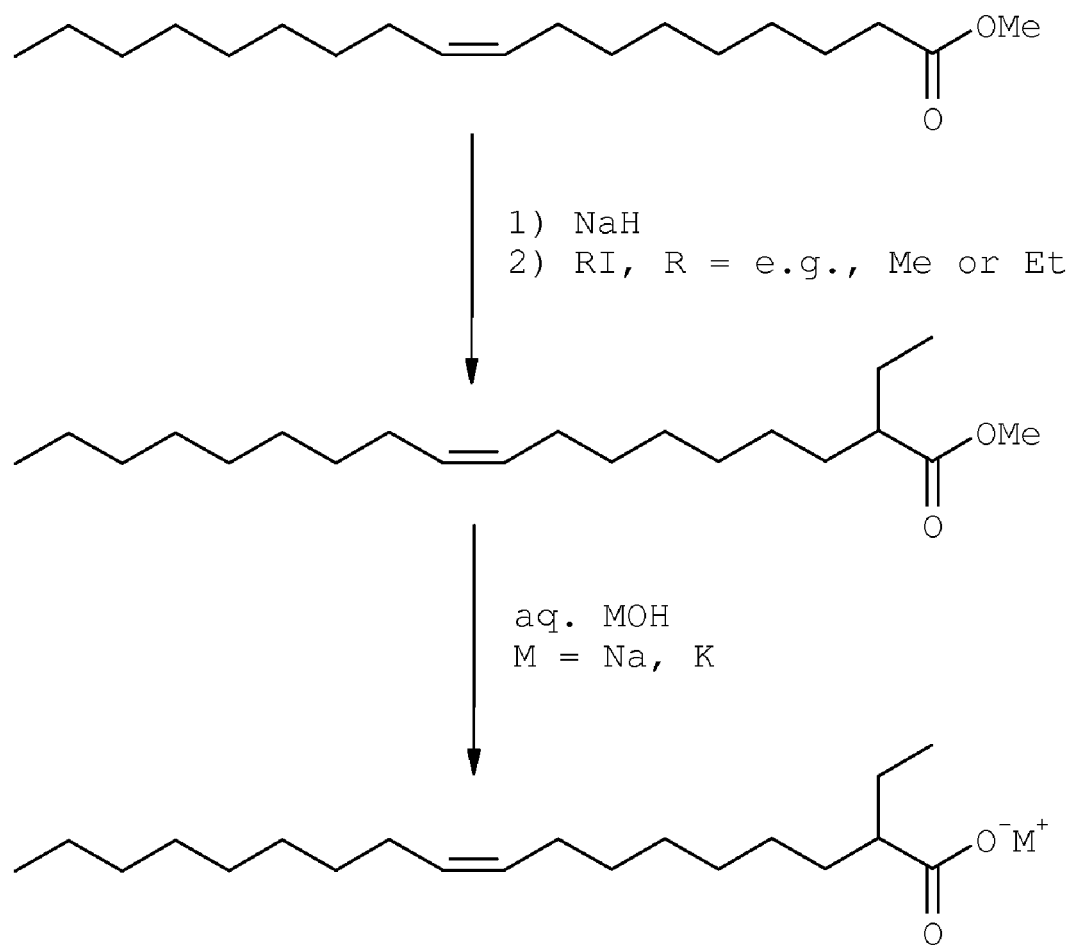
FIG. 1 shows schematically steps in the synthesis of an $\alpha$-branched fatty acid metal salt.
Figure 2:
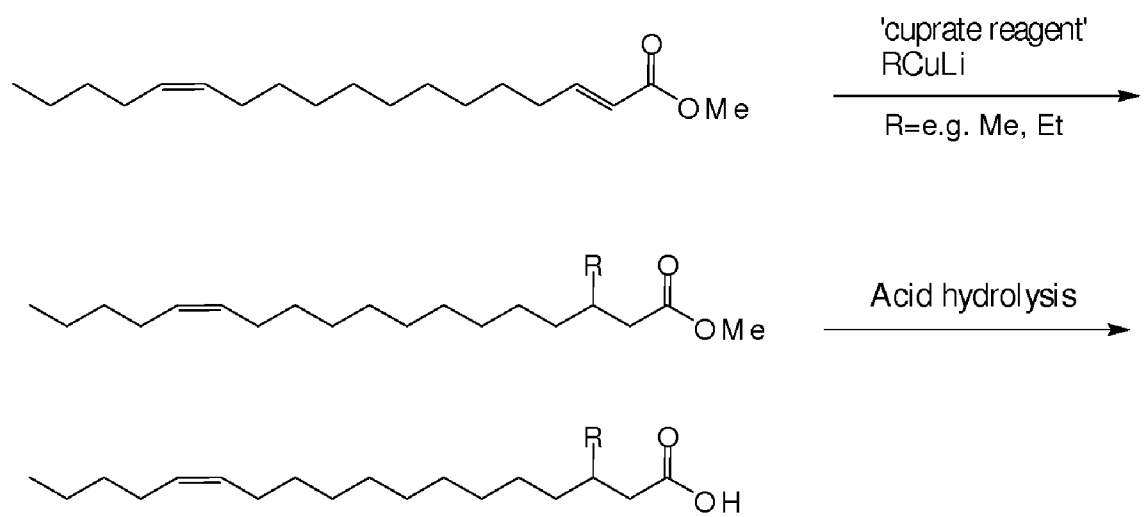
FIG. 2 shows schematically steps in the synthesis of a $\beta$-branched fatty acid metal salt.
Figure 3:
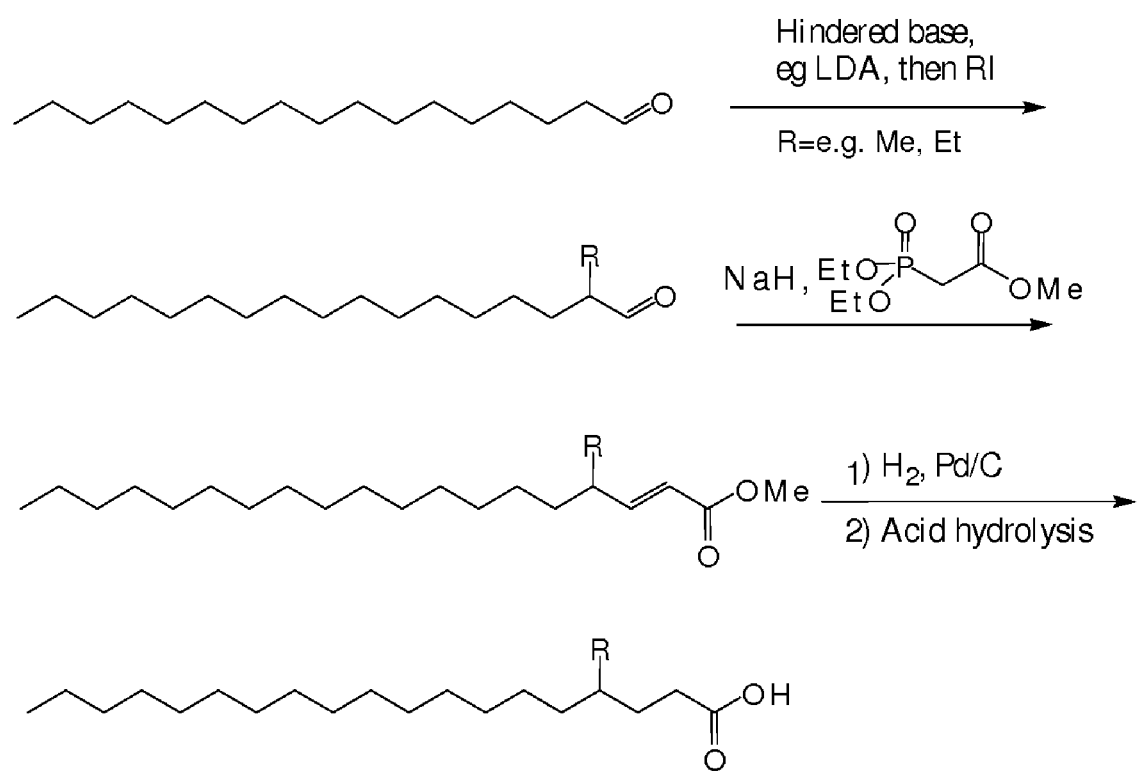
FIG. 3 shows schematically steps in the synthesis of a $\gamma$-branched fatty acid metal salt.

Synthetic routes to $\alpha$-, $\beta$- and $\gamma$-branched derivatives of various fatty acids are shown schematically in FIGS. 1 to 3. The type of fatty acid and length of side chain, R, can be varied. If desired, two side chains can be attached to the same fatty acid carbon atom.

A first step in a preparation of an $\alpha$-branched derivative of a $C_{10}$-$C_{25}$ straight chain acid is the formation of an $\alpha$-branch on the methyl ester of the acid. The $\alpha$-branched ester can then be saponified with metal hydroxide to generate the acid salt (and thence the acid, if required).

The following examples describes in more detail the preparation and characterisation of 2-methyl oleic acid.

1. Preparation of 2-Methyl Methyl Oleate

Sodium hydride (60% dispersion, 8 g, 0.2 mol) was washed with heptane (2×15 ml) and then suspended in tetrahydrofuran (THF) (300 ml). 1,3-dimethyl-3,4,5,6-tetrahydro-2(1H)-pyrimidinone (DMPU) (26 g, 0.2 mol) was added and the mixture was stirred under an atmosphere of nitrogen. Methyl oleate (67.46 ml, 0.2 mol) was added dropwise over a period of two hours and the resulting mixture was heated to reflux for 12 hours and then cooled to 0° C. Methyl iodide (0.2 mol) was then added dropwise and the reaction mixture was again heated to reflux for a further two hours. Next the reaction mixture was cooled to 0° C. and quenched with water (15 ml), concentrated in vacuo and purified by column chromatography ($SiO_2$, 1:9, diethyl ether:petroleum ether) to give 2-methyl methyl oleate as a yellow oil (50 g, 0.16 mol, 81%).

2. Preparation of 2-Methyl Oleic Acid

The 2-methyl methyl oleate from the above reaction (40 g, 0.13 mol) was dissolved in a (3:2:1) methanol, THF and water mixture (300 ml), and potassium hydroxide (14.4 g, 0.26 mol) was added and the reaction heated to reflux for 15 hours. The reaction mixture was then cooled and neutralised using dilute hydrochloric acid. The organic layer was separated and concentrated in vacuo, and was then purified by column chromatography (SiO2, (2:8) ethyl acetate:petroleum ether) to give 2-methyl oleic acid as an oil.

3. Characterisation

A rigid gel was formed when a 10% solution of potassium 2-methyl oleate (the potassium salt of the 2-methyl oleic acid prepared above) was mixed with an equal volume of a brine containing 16% KCl.

Contacting this gel with a representative hydrocarbon, such as heptane, resulted in a dramatic loss of viscosity and the formation of two low viscosity clear solutions: an upper oil phase and a lower aqueous phase. The formation of an emulsion was not observed. Thin-layer chromatography and infrared spectroscopy showed the presence of the branched oleate in both phases.

Figure 4:
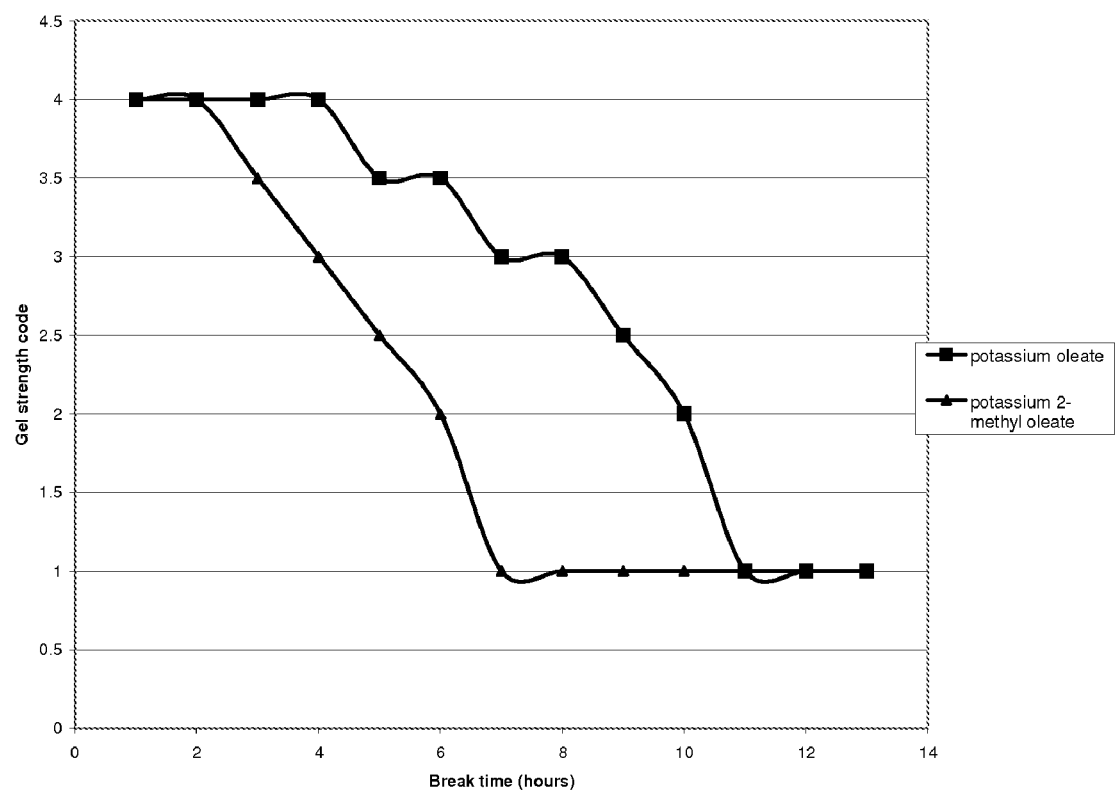
FIG. 4 shows a graph of gel strength against time for potassium oleate gel and potassium 2-methyl oleate gel.

The gel is apparently broken by a combination of micellar rearrangement and dissolution of the branched oleate in the oil phase. Consequently the breaking rate of the branched oleate is faster than that of the equivalent unbranched oleate. This is demonstrated in FIG. 4 which is a graph of gel strength against time at room temperature for a potassium oleate (unbranched) gel and the potassium 2-methyl oleate (branched) gel. Both gels were prepared from 10% solutions of the respective oleate mixed with equal volumes of a brine containing 16% KCl. Each gel was then contacted with an equal volume of heptane.

Gel strength is a semi-quantitative measure of the flowability of surfactant-based gel relative to the flowability of the precursor fluid before addition of the surfactant. There are four gel strength codings ranging from 1 (flowability of the original precursor fluid) to 4 (deformable, non-flowing gel). A particular gel is given a coding by matching the gel to one of the illustrations shown in FIG. 5.

Using infra-red spectroscopy, the value of $K_{ow}$ for the potassium 2-methyl oleate of the broken branched gel was measured as 0.11. In contrast the value of $K_{ow}$ for the potassium oleate of the broken unbranched gel was measured as effectively zero.

The rapid breakdown of the branched oleate surfactant gels, with little or no subsequent emulsion, leads to the expectation that these gels will be particularly suitable for use as wellbore fluids, such as fluids for hydraulic fracturing of oil-bearing zones. Excellent clean up of the fluids and reduced impairment of zone matrix permeability can also be expected because emulsion formation can be avoided.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A wellbore fluid configured for use in hydrocarbon recovery, comprising an aqueous solution of:

a surfactant, the surfactant in said solution consisting of a thickening amount of surfactant which is soluble in aqueous solutions and has the formula $(R_1-X)_n Z$, wherein:

$R_1$ is an aliphatic group comprising a $C_{16}$-$C_{24}$ principal straight chain bonded at a terminal carbon atom thereof to X, and comprising at least one $C_1$ or $C_2$ side chain; and X being a charged head group, Z being a counterion, and n being an integer which ensures that the surfactant is charge neutral; and wherein:

the charged head group X is selected to provide that the surfactant is soluble in oil; and at least one part of the charged head group is anionic wherein the wellbore fluid is a viscoelastic gel and wherein said gel undergoes a reduction in viscosity on contact with oil.

2. The wellbore fluid according to claim 1, wherein said side chain is bonded to the terminal carbon atom.

3. The wellbore fluid according to claim 1, wherein said principal straight chain is unsaturated.

4. The wellbore fluid according to claim 1, wherein said surfactant has a partition coefficient, $K_{ow}$, of at least 0.05.

5. The wellbore fluid according to claim 1 wherein said side chain is bonded to said principal straight chain at a carbon atom of said straight chain selected from its said terminal carbon atom, the neighbouring carbon atom and the next neighbouring carbon atom.

* * * * *